US011661385B2

(12) United States Patent
Funk et al.

(10) Patent No.: US 11,661,385 B2
(45) Date of Patent: May 30, 2023

(54) PROCESS FOR INCREASING THE CONCENTRATION OF NORMAL HYDROCARBONS IN A LIGHT NAPHTHA STREAM

(71) Applicant: UOP LLC, Des Plaines, IL (US)

(72) Inventors: Gregory Funk, Carol Stream, IL (US); Stephen W. Sohn, Arlington Heights, IL (US); Cora Wang Ploentham, Elk Grove Village, IL (US); Nikunj Patel, West Chicago, IL (US); Hari S. Bajpai, Gurgaon (IN); Manoj Kumar, Gurgram (IN)

(73) Assignee: UOP LLC, Des Plaines, IL (US)

(*) Notice: Subject to any disclaimer, the term of this patent is extended or adjusted under 35 U.S.C. 154(b) by 0 days.

(21) Appl. No.: 17/188,682

(22) Filed: Mar. 1, 2021

(65) Prior Publication Data

US 2022/0274899 A1 Sep. 1, 2022

(51) Int. Cl.
| | |
|---|---|
| C07C 5/27 | (2006.01) |
| C07C 4/04 | (2006.01) |
| C07C 7/04 | (2006.01) |
| C07C 7/12 | (2006.01) |
| C07C 7/00 | (2006.01) |
| B01D 3/14 | (2006.01) |
| B01D 15/20 | (2006.01) |

(52) U.S. Cl.
CPC ............... *C07C 5/27* (2013.01); *B01D 3/143* (2013.01); *B01D 15/203* (2013.01); *C07C 4/04* (2013.01); *C07C 7/005* (2013.01); *C07C 7/04* (2013.01); *C07C 7/12* (2013.01)

(58) Field of Classification Search
None
See application file for complete search history.

(56) References Cited

U.S. PATENT DOCUMENTS

| | | | |
|---|---|---|---|
| 3,291,726 A | 12/1966 | Broughton | |
| 4,006,197 A | 2/1977 | Bieser | |
| 4,608,061 A * | 8/1986 | Voiles | C07C 7/12 95/143 |
| 6,897,345 B2 | 5/2005 | Marchionna et al. | |
| 9,302,956 B2 * | 4/2016 | Lapinski | C07C 7/04 |
| 9,302,957 B2 | 4/2016 | Lapinski | |

(Continued)

OTHER PUBLICATIONS

Search Report and Written Opinion dated Jun. 2, 2022.

*Primary Examiner* — Tam M Nguyen
(74) *Attorney, Agent, or Firm* — Paschall & Associates, LLC; James C. Paschall

(57) ABSTRACT

A process increases the concentration of normal paraffins in a feed stream comprising separating a naphtha feed stream into a normal paraffin rich stream and a non-normal paraffin rich stream. A naphtha feed stream may be separated into a normal paraffin stream and a non-normal paraffin stream. An isomerization feed stream may be taken from the non-normal paraffin stream and isomerized over an isomerization catalyst to convert non-normal paraffins to normal paraffins and produce an isomerization effluent stream. The isomerization effluent stream may be separated into a propane stream and a C4+ hydrocarbon stream optionally in a single column. The C4+ hydrocarbon stream may be recycled to the step of separating a naphtha feed stream.

19 Claims, 4 Drawing Sheets

(56) References Cited

U.S. PATENT DOCUMENTS

| | | | |
|---|---|---|---|
| 9,302,959 B2 | 4/2016 | Lapinski | |
| 9,302,960 B2 | 4/2016 | Lapinski | |
| 11,021,422 B1* | 6/2021 | Koseoglu | C07C 4/04 |
| 2004/0249230 A1* | 12/2004 | Gillespie | B01J 23/63 |
| | | | 585/743 |
| 2014/0171704 A1* | 6/2014 | Erisken | C10G 55/04 |
| | | | 585/303 |
| 2015/0315100 A1* | 11/2015 | Lapinski | C07C 7/005 |
| | | | 585/737 |
| 2015/0315101 A1 | 11/2015 | Lapinski | |
| 2015/0315102 A1* | 11/2015 | Lapinski | C07C 4/04 |
| | | | 585/737 |
| 2016/0185688 A1 | 6/2016 | Lapinski | |
| 2018/0155642 A1* | 6/2018 | Al-Ghamdi | C10G 69/08 |
| 2019/0161691 A1* | 5/2019 | Ghosh | C10G 31/08 |
| 2021/0277316 A1* | 9/2021 | Funk | C10G 63/04 |
| 2023/0036734 A1* | 2/2023 | Lapinski | C10G 35/06 |

* cited by examiner

PROCESS FOR INCREASING THE CONCENTRATION OF NORMAL HYDROCARBONS IN A LIGHT NAPHTHA STREAM

FIELD

The field is processes for increasing the concentration of normal hydrocarbons in a feed stream.

BACKGROUND

Ethylene and propylene are important chemicals for use in the production of other useful materials, such as polyethylene and polypropylene. Polyethylene and polypropylene are two of the most common plastics found in use today and have a wide variety of uses. Uses for ethylene and propylene include the production of vinyl chloride, ethylene oxide, ethylbenzene and alcohol.

The great bulk of the ethylene consumed in the production of the plastics and petrochemicals such as polyethylene is produced by the thermal cracking of higher molecular weight hydrocarbons. Steam is usually mixed with the feed stream to the cracking furnace to reduce the hydrocarbon partial pressure and enhance olefin yield and to reduce the formation and deposition of carbonaceous material in the cracking reactors. The process is therefore often referred to a steam cracking or pyrolysis.

The composition of the feed to the steam cracking reactor affects the product distribution. The propensity of particular hydrocarbons to crack is greater than others. The tendency of the hydrocarbons to crack to ethylene normally ranks in the following order: normal paraffins; iso-paraffins; olefins; naphthenes; and aromatics. Benzene and other aromatics are particularly resistant to steam cracking and undesirable as cracking feed stocks, with only the alkyl side chains being cracked to produce the desired product.

The feed to a steam cracking unit is also normally a mixture of hydrocarbons varying both by type of hydrocarbon and carbon number. This variety makes it difficult to separate less desirable feed components, such as naphthenes and aromatics, from the feed stream by fractional distillation. The normal paraffins and the non-normal paraffins can be separated by an adsorption process. Increasing the concentration of normal paraffins in a stream can improve the quality of a feedstock to the steam cracking unit.

Common feeds to steam crackers include light naphtha, which is concentrated in C5-C6 hydrocarbons, and LPG, which comprises C3-C4 hydrocarbons. Light naphtha streams typically contain a mixture of n-paraffins, iso-paraffins, naphthenes and aromatics. It is generally not possible to procure light naphtha streams that are concentrated in n-paraffins. Similarly, LPG streams typically contain a mixture of n-butane, iso-butane, and propane, but streams concentrated in n-butane are not commonly available.

One way to upgrade light naphtha is first to separate the naphtha into a normal paraffin rich stream and a non-normal paraffin rich stream; and subsequently convert a substantial amount of the non-normal paraffin stream in an isomerization zone in the presence of a catalyst into normal paraffins. Isomerization can produce normal butanes with the other normal paraffins which must be managed. Separating isoparaffins intended for further isomerization from normal paraffins intended for steam cracking requires a series of fractionation columns and can substantially increase capital cost.

An efficient process for separating and converting the iso-paraffins in light naphtha to normal paraffins would significantly increase the profitability of steam cracking operations by increasing the yield of high value ethylene and propylene.

BRIEF SUMMARY

A process increases the concentration of normal paraffins in a feed stream comprising separating a naphtha feed stream into a normal paraffin rich stream and a non-normal paraffin rich stream. An isomerization feed stream may be taken from the non-normal paraffin stream and isomerized over an isomerization catalyst to convert non-normal paraffins to normal paraffins and produce an isomerization effluent stream. The isomerization effluent stream may be separated into a propane stream and a C4+ hydrocarbon stream optionally in a single column. The C4+ hydrocarbon stream may be recycled to the step of separating a naphtha feed stream.

Additional details and embodiments of the invention will become apparent from the following detailed description of the invention.

DETAILED DESCRIPTION

The present disclosure endeavors to separate normal paraffins from a light naphtha stream comprising C4-C7 paraffins for an ideal steam cracker feed. The process employs a separation of normal paraffins from non-normal hydrocarbons to extract normal paraffins from the light naphtha stream and may transport the normal paraffins to a steam cracking unit. Furthermore, the non-normal hydrocarbons are converted to normal paraffins and may also be transported to a steam cracking unit. The non-normal hydrocarbons, which include iso-paraffins, naphthenes and aromatics, can optionally undergo an additional separation to separate isobutanes, isopentanes and isohexanes from the C6 cyclics and any C7+ hydrocarbons from the isopentanes and isohexanes. The isobutanes, isopentanes and isohexanes can be isomerized to increase the concentration of normal paraffins and then be subjected to separation. Mixed C4+ paraffins from isomerization can be recycled back to the normal-non-normal separation without having to separate isobutanes from normal butanes in a dedicated fractionation column. Optionally, a deisobutanizer column may separate isobutanes from C4+ paraffins and be recycled to the isomerization zone.

The term "Cx" is to be understood to refer to molecules having the number of carbon atoms represented by the subscript "x". Similarly, the term "Cx−" refers to molecules that contain less than or equal to x and preferably x and less carbon atoms. The term "Cx+" refers to molecules with more than or equal to x and preferably x and more carbon atoms.

Figure 1:
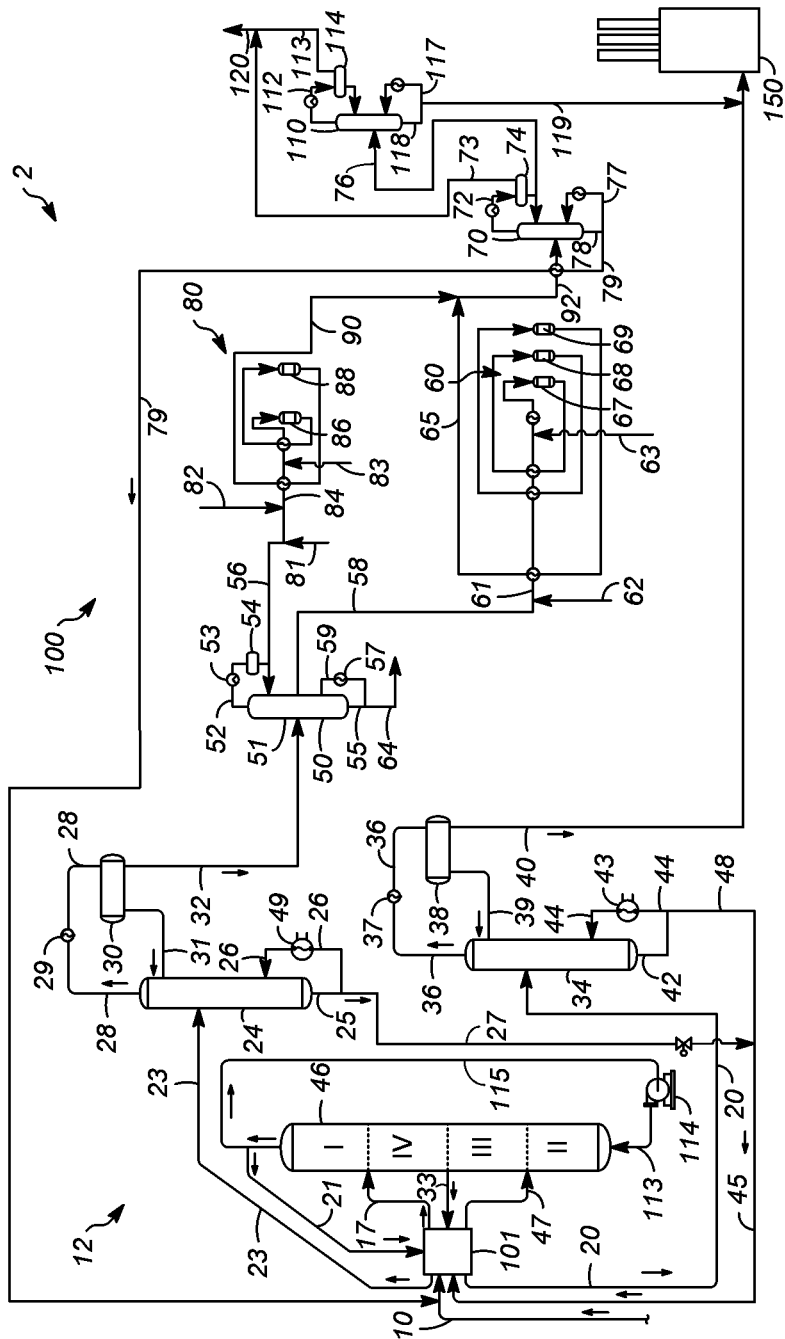
FIG. 1 is a schematic view of a conversion unit of the present disclosure.

In the process and apparatus 2 in FIG. 1, a naphtha feed stream in line 10 is preferably a hydrotreated light naphtha stream comprising substantially C4 to C6 hydrocarbons having a T90 between about 40° C. and about 90° C. The end point is taken to minimize the presence of hydrocarbons with more than six carbon atoms in the feed. Suitably no more than about 30 wt % C7+ hydrocarbons, preferably no more than about 20 wt % C7+ hydrocarbons and more preferably no more than about 10 wt % C7+ hydrocarbons can be present in the light naphtha feed stream. The naphtha feed stream may comprise normal paraffins, iso-paraffins, naphthenes, and aromatics.

We have found that normal paraffins yield more light olefins in a steam cracking unit. Hence, it is desired to increase the concentration of normal paraffins in the feed stream 10. The first step in the process is a step of separating the naphtha feed stream into a normal paraffin-rich stream and a non-normal paraffin-rich stream. Normal molecules are defined to mean straight chain molecules such as normal butane, normal hexane, and normal pentane. The most efficient process for such a separation utilizes adsorption. In an aspect, an adsorbent separation unit 12 is used to separate normal paraffins from non-normal paraffins.

As used herein, the term "a component-rich stream" or "a component stream" means that the stream coming out of a vessel has a greater concentration of the component than the feed to the vessel. As used herein, the term "a component-lean stream" means that the lean stream coming out of a vessel has a smaller concentration of the component than the feed to the vessel.

The naphtha feed stream is delivered to the process in a feed line 10 and passed to the adsorbent separation unit 12. The feed stream in feed line 10 is passed through a valve 101 in the adsorbent separation unit 12 which delivers the feed to an appropriate bed in an adsorbent vessel 46.

The feed stream in feed line 10 is separated into a normal paraffins stream and a non-normal paraffins stream. Normal paraffins of the naphtha mixture selectively enter or occlude into the porous structure of the adsorbent components but branched or cyclic non-normal chain paraffins do not typically enter the pores. The non-normal paraffins exit the process as a raffinate stream. In an aspect, the normal butanes enter or occlude into the porous structure of the adsorbent components while the non-normal butanes do not typically enter the pores in addition to the same dynamic for the C5-C7 paraffins. Consequently, the butanes are separated in the adsorbent separation unit 12 like the C5-C7 hydrocarbons.

To provide a useful method for separation of normal from non-normal paraffins, it is necessary to desorb the occluded normal paraffins. In the disclosed process, normal nonane or normal decane or even heavier normal paraffin can suitably be used as a desorbent to desorb normal paraffins in an extract-desorbent stream.

The adsorbent used in the adsorption vessel preferably comprises aluminosilicate molecular sieves having relatively uniform pore diameters of about 5 Angstroms. The preferred adsorbent is provided by commercially available type 5A molecular sieves produced and sold by UOP LLC in Des Plaines, Ill.

The adsorbent vessel 46 may comprise a series of vertically spaced, separate beds interconnected by a pipe 115 between the bottom of one bed and the top of its upstream adjacent bed. The valve 101 may comprise a manifold arrangement or a rotary valve for advancing the points of inlet and outlet of respective streams in a downstream direction. The adsorbent vessel 46 operates in an upflow mode, although downflow may be suitable. The adsorbent vessel 46 is shown to have four beds I-IV for simplicity, but it may have more beds such as eight, twelve or twenty-four beds.

The feed stream is introduced through feed line 10 through valve 101 which is positioned to send the feed stream through line 17 into the adsorbent bed I. The extract and desorbent is withdrawn from a top of the desorption bed III in line 33, transported through the valve 101 in an extract line 20 to an extract fractionation column 34 to separate desorbent from extract. The desorbent is introduced through desorbent line 45 through the valve 101 which is positioned to send the desorbent through a desorbent line 47 into the bottom of the desorbent bed III. The raffinate is withdrawn from a top of the adsorption bed I through a raffinate line 21, through valve 101 and through line 23 to the raffinate fractionation column 24.

Simulated countercurrent flow is achieved by periodically advancing downstream the point of introducing the feed stream and the desorbent while simultaneously and equally advancing downstream the point of withdrawal of raffinate and extract. The adsorbent bed I is defined as the zone bounded between the feed stream inlet and the raffinate outlet; the primary rectification bed II is defined as the zone bounded between the raffinate outlet and the desorbent inlet; the desorption bed III is defined as the zone bounded between the desorbent inlet and the extract outlet; and the secondary rectification bed IV is defined as the zone bounded between the extract outlet and the feed stream inlet. Typical liquid phase operation is preferred, for example, at temperatures of the from about 50° C. to about 300° C., and more particularly no more than about 260° C., and pressures of from slightly superatmospheric to about 30 atmospheres.

Raffinate, characterized as less adsorbed in the adsorption vessel, is withdrawn from the adsorption vessel 46 in the raffinate line 21 through the valve 101 and enters the raffinate fractionation column 24 through line 23. Since it is desired to obtain a normal paraffin product, the raffinate fractionation column 24 is operated to separate two fractions, a raffinate overhead stream rich in non-normal paraffins, in an embodiment, rich in C7– non-normal paraffins, and a desorbent bottoms stream rich in normal paraffin desorbent, in an embodiment, rich in C9+ normal paraffins. The raffinate overhead stream is withdrawn from the raffinate fractionation column 24 in an overhead line 28, condensed in a cooler 29 and fed to a separator 30. A portion of the condensed raffinate overhead is recycled to the raffinate fractionation column 24 as reflux through a reflux line 31 and the remaining portion of the condensed raffinate overhead is withdrawn through a net raffinate overhead line 32. The raffinate overhead stream is rich in non-normal C7– paraffins which can be transported to the isomerization zone 100. Alternatively, the raffinate overhead stream in the overhead line 28 may be fully condensed and fully refluxed in line 31 and the raffinate stream in line 32 be taken in a side cut from the raffinate column 24.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripper columns may omit a reboiler at a bottom of the column and instead provide heating requirements and separation impetus from a fluidized inert media such as steam. Stripping columns typically feed a top tray and take main product from the bottom.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

The raffinate bottoms stream is withdrawn from the raffinate fractionation column 24 through a bottoms line 25 where a portion of the raffinate bottoms stream flows through a reboiler line 26, reboiler heater 49 and returns heated to the raffinate fractionation column 24. The remaining portion of said raffinate bottoms stream flows through a net bottoms line 27 as a normal paraffin rich stream, particularly rich in normal C9+ paraffins. The raffinate bottoms stream comprising a raffinate desorbent stream in line 27 can be recycled to the adsorption vessel 46 in the desorbent line 45 perhaps after joining an extract bottoms stream in line 48. The raffinate fractionation column 24 operates in a bottoms temperature range of about 250 to about 290° C. and an overhead pressure of about 450 to about 550 kPa (gauge).

Extract is more or selectively adsorbed on the adsorbent in the adsorption vessel 46. The desorbent displaces the selectively adsorbed normal paraffins from the solid adsorbent in desorbent bed III of adsorbent vessel 46. The extract and desorbent are withdrawn in line 33, and the valve 101 connects line 33 with line 20. Extract and desorbent withdrawn from the adsorption vessel in the extract line 33 connected through the valve 101 is directed in line 20 to the extract fractionation column 34. Since it is desired to obtain a normal paraffin product, the extract fractionation column 34 is operated to separate two fractions, an extract overhead stream rich in normal paraffins, in an embodiment, rich in C4-C7 normal paraffins, and a desorbent bottoms stream rich in normal paraffin desorbent, in an embodiment, rich in C9+ normal paraffins. The extract overhead stream is withdrawn from the extract fractionation column 34 in an overhead line 36, condensed in a cooler 37 and fed to a separator 38. A portion of the condensed extract overhead is recycled to the extract fractionation column 34 as reflux through a reflux line 39 and the remaining portion of the condensed extract overhead is withdrawn through a net extract overhead line 40. The extract overhead stream is rich in C4-C7 normal paraffins which can be recovered or taken as steam cracker feed and fed to the steam cracker unit 150 in line 40.

The extract bottoms stream is withdrawn from extract fractionation column 34 through a bottoms line 42 where a portion of the extract bottoms stream flows through a reboiler line 44, reboiler heater 43 and returns heated to the extract fractionation column 34. A remaining portion of the extract bottoms stream flows through line 48 as a normal paraffin rich stream, particularly rich in normal C9+ paraffins. The extract bottoms stream in line 48 comprising an extract desorbent stream can join the raffinate bottoms stream in line 27 comprising a raffinate desorbent stream. Both can be recycled in the desorbent line 45 through the valve 101 to the adsorption vessel 46 in the desorbent line 47. The extract fractionation column 34 operates in bottoms temperature range of about 225 to about 275° C. and an overhead pressure of about 250 to about 350 kPa (gauge).

The non-normal paraffin rich stream particularly rich in non-normal C4 to C7 paraffins can be isomerized to increase the concentration of normal C4 to C7 paraffins to equilibrium levels. However, it has been discovered that the conversion to normal paraffins in an isomerization zone 100 can be increased by removing a portion of the C6 cyclic hydrocarbons, such as cyclohexane, methylcyclopentane, and benzene, in the isomerization feed stream passing into the isomerization zone 100. Specifically, when the concentration of C6 cyclic hydrocarbons in the stream has been reduced, disproportionation reactions occur which lead to increased amounts of valuable propane and butanes, as well as increases in the per pass conversion of the iso-paraffin hydrocarbons in the feed to normal paraffins. The products from the disproportionation reactions undergo isomerization reactions leading to an increase in yields of normal paraffins. Furthermore, additional conversion to C2 to C4 normal paraffins in the non-normal paraffin rich stream is accomplished via hydrocracking reactions in the isomerization zone 100. We have surprisingly found that naphthenes and aromatics fed to the isomerization zone 100 under the more severe conditions will undergo ring opening and be converted to n-paraffins.

In an embodiment, the process may install a raffinate splitter column 50 downstream of the adsorbent separation vessel 46 to separate the net raffinate overhead stream comprising non-normal paraffins in line 32 into an isobutane stream and an isopentane stream. The isopentane stream may also be rich in isohexane and be an isohexane stream. The isopentane and/or isohexane stream may be characterized as a higher isoalkane stream. The net raffinate overhead stream comprising non-normal paraffins in line 32 may also be separated into a C6 cyclic and C7+ hydrocarbons stream in the raffinate splitter column 50. Since the non-normal paraffin stream in line 32 contains little n-hexane with a normal boiling point of 69° C. because it is removed in the adsorption separation vessel 46, the separation of C6 cyclics from iso-paraffins is simplified. The lightest C6 cyclic hydrocarbon is methylcyclopentane having a normal boiling point of 72° C. whereas iso-C6 paraffins normally boil at 50-64° C. Hence, the proper ordering of separation steps obviates a difficult split between normal hexane and methylcyclopentane that would be capitally and operationally intensive and result in a loss of much of the normal hexane, which is a valuable steam cracker feed.

The raffinate splitter overhead stream in the raffinate splitter net overhead line 56 separated from the non-normal paraffin stream in line 32 is rich in isobutanes and can be termed an isobutane stream. The isobutane stream is withdrawn in a raffinate splitter overhead line 52 from an overhead of the raffinate splitter column 50 and passed through a cooler 53 and into a separator 54. A portion of the raffinate splitter overhead stream is recycled to the raffinate splitter column 50 as reflux through a reflux line and the remaining portion of the raffinate splitter overhead stream is withdrawn in a net raffinate splitter overhead line 56. The raffinate splitter overhead stream is rich in isobutane. The isobutane stream taken in the net raffinate splitter overhead line 56 from the non-normal paraffin stream in line 32 may be charged as a first isomerization feed stream to a first isomerization unit 80 to increase its normal-butane concentration.

The raffinate splitter side stream taken in an intermediate line 58 may be rich in isopentanes and can be termed as an isopentane stream. The raffinate splitter side stream taken in an intermediate line 58 may also be rich in isohexanes and be termed as an isohexane stream. The raffinate splitter side stream can be termed a higher isoalkane stream because it is rich in isopentane and/or isohexane. The raffinate splitter side stream comprising higher isoalkanes is withdrawn from a side 51 of the raffinate splitter column 50 in the intermediate line 58. The higher isoalkane stream may be taken in the intermediate line from the side 51 of the raffinate splitter column 50 from the non-normal paraffin stream in the net raffinate overhead line 32 and fed as a second, higher isoalkane isomerization feed stream to a second, higher isomerization unit 60 to increase its normal alkane concentration. Particularly, the higher isomerization unit 60 increases the concentration of normal pentanes and/or normal hexanes.

The raffinate splitter bottoms stream is withdrawn from raffinate splitter column 50 through a bottoms line 55 from which a portion of the raffinate splitter bottoms flows through a reboiler line 59, a reboiler heater 57 and returns to the raffinate splitter column 50. The remaining portion of the raffinate splitter bottoms stream flows through a net splitter bottoms line 64 as a cyclic hydrocarbon stream rich in cyclic C6 hydrocarbons and benzene and particularly rich in methylcyclopentane. The cyclic paraffins stream in the net splitter bottoms line 64 can be taken to a reforming unit to produce aromatic hydrocarbons or sent to the steam cracker 150. Any C4+ hydrocarbons produced from steam cracking or reforming the cyclic paraffins stream can be recycled to the adsorption separation unit 12. The raffinate splitter column 50 operates in bottoms temperature range of about 124 to about 154° C. and an overhead pressure range of about 0 to about 138 kPa (gauge).

The isobutane stream in the net raffinate splitter overhead line 56 may be combined with a first hydrogen stream in a first hydrogen line 82 and optionally a fresh isobutane stream in a fresh isobutane line 81 to provide an isobutane isomerization feed stream in an isobutane isomerization feed line 84. The isobutane isomerization feed stream is heated by heat exchange with an isobutane isomerization effluent stream and isomerized in a first, butane isomerization unit 80. In the butane isomerization unit 80, the isobutane paraffins, in the presence of hydrogen provided by the hydrogen line 83 and a butane isomerization catalyst, are converted into normal butane to attain equilibrium levels of normal butane.

In addition to isobutane-normal butane isomerization, the conversion of isobutane via disproportionation reactions can also occur. The isobutanes can react via disproportionation to form propane and a pentane. The isopentanes can also isomerize to equilibrium producing normal pentane. Thus, there is an increase in the overall yield of the normal paraffins to propane, normal butane and normal pentane in the butane isomerization unit 80.

The butane isomerization catalyst in the butane isomerization unit 80 may include chlorided alumina, sulfated zirconia, tungstated zirconia or zeolite-containing isomerization catalysts. The butane isomerization catalyst may be amorphous, e.g., based upon amorphous alumina, or zeolitic. A zeolitic catalyst would still normally contain an amorphous binder. The butane isomerization catalyst may comprise a sulfated zirconia and platinum as described in U.S. Pat. No. 5,036,035 and EP 0666109 A1 or a platinum group metal on chlorided alumina as described in U.S. Pat. Nos. 5,705,730 and 6,214,764. Another suitable catalyst is described in U.S. Pat. No. 5,922,639. U.S. Pat. No. 6,818,589 discloses a catalyst comprising a tungstated support of an oxide or hydroxide of a Group IVB (IUPAC 4) metal, preferably zirconium oxide or hydroxide, at least a first component which is a lanthanide element and/or yttrium component, and at least a second component being a platinum-group metal component. An advantage of a non-chlorided catalyst, such as a sulfated zirconia catalyst, is the absence of chloride omitting further treatment of the effluent streams from the butane isomerization unit 80. If chlorided alumina catalyst is used as the butane isomerization catalyst, a chloriding agent in line 83 will be added to the butane isomerization feed stream 84.

The butane isomerization conditions in the butane isomerization unit 80 include reactor temperatures ranging from about 40° C. to about 250° C., preferably at reactor temperatures ranging from 90° C. to 230° C. Reactor operating pressures generally range from about 100 kPa to 10 MPa absolute. Liquid space velocity ranges from about 0.2 to about 25 volumes of hydrocarbon feed per hour per volume of catalyst. Hydrogen is admixed with the butane isomerization feed to the butane isomerization unit 80 to provide a mole ratio of hydrogen to hydrocarbon feed of from about 0.01 to 20. The hydrogen may be supplied totally from outside the process or supplemented by hydrogen recycled to the feed after separation from the butane isomerization reactor effluent.

Contacting within the butane isomerization unit 80 may be effected using the catalyst in a fixed-bed system, a moving-bed system, a fluidized-bed system, or in a batch-type operation. The reactants may be contacted with the bed of catalyst particles in upward, downward, or radial-flow fashion. The reactants may be in the liquid phase, a mixed liquid-vapor phase, or a vapor phase when contacted with the catalyst particles, with a mixed phase or vapor phase being preferred. The butane isomerization unit 80 may be in a single reactor 86 or two or more separate reactors 86 and 88 with suitable means therebetween to ensure that the desired isomerization temperature is maintained at the entrance to each zone. Even though the main reaction in the butane isomerization unit is isomerization of isoparaffins to normal paraffins which is endothermic, sufficient exothermic hydrogenation reactions occur causing the temperatures across the reactors to increase. Consequently, the butane isomerization effluent from an upstream reactor 86 must be cooled before going to a downstream reactor 88. For example, a first butane isomerate stream from a first butane isomerization reactor 86 may be cooled by heat exchange with the butane isomerization feed stream in line 84 and fed to a second butane isomerization reactor 88. Moreover, a second butane isomerate stream from the second butane isomerization reactor 88 may be heat exchanged with the butane isomerization feed stream comprising an isobutane-rich stream mixed with hydrogen to cool the second butane isomerate and cool the butane isomerization feed stream upstream of the heat exchange with the first butane isomerate stream. Two or more reactors in sequence enable improved isomerization through control of individual reactor temperatures and partial catalyst replacement without a process shutdown. A first, butane isomerization effluent stream comprising an increased concentration of normal paraffins exits the last reactor in the butane isomerization unit 80 in a butane isomerization effluent line 90. The butane isomerization effluent stream in line 90 may be fed to a depropanizer column 70 in a depropanizer feed line 92 after it is combined with a second isomerization effluent stream in line 65.

The non-normal, non-cyclic paraffin rich stream in the intermediate raffinate splitter line 58 may be combined with a hydrogen stream in a higher hydrogen line 62 and heated by heat exchange with reactor effluent and fed to a higher isomerization unit 60. In the higher isomerization unit 60, isopentane and/or isohexane, in the presence of hydrogen provided by hydrogen line 62 and a higher isomerization catalyst, are converted to increase the concentration of normal paraffins: ethane, propane, normal butane, normal pentane and normal hexane. Three reactions promote the production of normal paraffin-iso-paraffin disproportionation reactions, opening of aromatics and cyclics, reverse isomerization of iso-paraffins, and paraffin hydrocracking reactions.

Cracking of some of the paraffins can occur in the higher isomerization unit 60 to produce C4– paraffins. Moreover, the conversion of isopentane and/or isohexane increases significantly via disproportionation reactions because the non-normal, non-cyclic paraffin rich stream in the intermediate raffinate splitter line 56 is passed into the higher isomerization unit 60 lean in cyclic C6 hydrocarbons. It is believed that the paraffin disproportionation reactions occur by the combination of two iso-paraffins followed by scission into one lighter hydrocarbon and one heavier hydrocarbon. For example, two isopentanes can combine and form an isobutane and an isohexane in the presence of hydrogen. The isobutanes can further react via disproportionation to form a propanes and isopentanes. A portion of the produced isobutanes also converts to normal butanes via isomerization reactions in the isomerization zone. Production of normal propane and butane via disproportionation and isomerization reactions occurs with low production of low-value undesired methane as a cracked product. Thus, there is an increase in the overall yield of the normal paraffins in the first isomerization unit 60.

In the higher isomerization unit 60, hydrocracking of the isopentane and/or isohexane occurs to produce methane, ethane, propane, and isobutane. The isobutane can further react via disproportionation reactions and/or isomerization to further produce normal paraffins.

The higher isomerization catalyst in the higher isomerization unit 60 may include chlorided alumina, sulfated zirconia, tungstated zirconia or zeolite-containing isomerization catalysts. The higher isomerization catalyst may be amorphous, e.g., based upon amorphous alumina, or zeolitic. A zeolitic catalyst would still normally contain an amorphous binder. The catalyst may comprise a sulfated zirconia and platinum as described in U.S. Pat. No. 5,036,035 and EP 0666109 A1 or a platinum group metal on chlorided alumina as described in U.S. Pat. Nos. 5,705,730 and 6,214,764. Another suitable catalyst is described in U.S. Pat. No. 5,922,639. U.S. Pat. No. 6,818,589 discloses a catalyst comprising a tungstated support of an oxide or hydroxide of a Group IVB (IUPAC 4) metal, preferably zirconium oxide or hydroxide, at least a first component which is a lanthanide element and/or yttrium component, and at least a second component being a platinum-group metal component. An advantage of a non-chlorided catalyst, such as a sulfated zirconia catalyst, is the absence of chloride omitting further treatment of the effluent streams from the isomerization unit 60. If chlorided alumina catalyst is used as the isomerization catalyst, a chloriding agent in line 63 will be added to the higher isomerization feed stream 61.

The higher isomerization process conditions in the higher isomerization unit 60 include an average reactor temperature usually ranging from about 40° to about 250° C. Reactor operating pressures generally range from about 100 kPa to 10 MPa absolute. Liquid hourly space velocities (LHSV) range from about 0.2 to about 25 volumes of hydrocarbon feed per hour per volume of catalyst. Hydrogen is admixed with or remains with the higher isomerization feed to the higher isomerization unit to provide a mole ratio of hydrogen to hydrocarbon feed of from about 0.01 to 20. The hydrogen may be supplied totally from outside the process or supplemented by hydrogen recycled to the feed after separation from higher isomerization reactor effluent.

Contacting within the higher isomerization unit 60 may be effected using the higher isomerization catalyst in a fixed-bed system, a moving-bed system, a fluidized-bed system, or in a batch-type operation. The reactants may be contacted with the bed of higher isomerization catalyst particles in upward, downward, or radial-flow fashion. The reactants may be in the liquid phase, a mixed liquid-vapor phase, or a vapor phase when contacted with the higher isomerization catalyst particles, with a mixed phase or vapor phase being preferred. The higher isomerization unit 60 may be in a single reactor 66 or in two or more separate higher isomerization reactors 67, 68, and 69 with suitable means therebetween to ensure that the desired isomerization temperature is maintained at the entrance to each reactor.

The reactions in the higher isomerization unit 60 generate an exotherm across the reactors so the higher isomerization effluent streams need to be cooled between reactors. For example, a first higher isomerate stream from a first isomerization reactor 67 may be heat exchanged with the higher isomerization feed stream in the higher isomerization feed line 61 comprising the non-normal, non-cyclic paraffin rich stream mixed with hydrogen to cool the higher isomerate and heat the higher isomerization feed stream. Moreover, a second higher isomerate stream from a second higher isomerization reactor 68 may be heat exchanged with the higher isomerization feed stream comprising the non-normal, non-cyclic paraffin rich stream mixed with hydrogen upstream of the heat exchange with the first higher isomerate steam to cool the higher isomerate stream and heat the higher isomerization feed stream. Additionally, a third isomerate stream from the third isomerization reactor 69 may be heat exchanged with the higher isomerization feed stream comprising non-normal, non-cyclic paraffin rich stream mixed with hydrogen upstream of the heat exchange with the second higher isomerate stream to cool the higher isomerate and heat the higher isomerization feed stream. Since hydrocracking reactions are accompanied by hydrogenation reactions that are very exothermic, two to five higher isomerization reactors in sequence enable improved control of individual reactor temperatures and partial catalyst replacement without a process shutdown. A higher isomerization effluent stream comprising an increased concentration of normal paraffins exits the last higher isomerization reactor 69 in the higher isomerization unit 60 in a higher isomerization effluent line 65.

A depropanizer column 70 separates a higher isomerization effluent stream in line 65 into a depropanizer overhead stream comprising propane and a depropanized bottoms stream comprising C4+ paraffins in a single fractionation column. In an embodiment, a depropanizer column 70 separates the higher isomerization effluent stream in line 65 and a butane isomerization effluent stream in line 90 into a depropanizer overhead stream comprising propane and a depropanized bottoms stream comprising C4+ paraffins in a single fractionation column. Line 92 may take the higher isomerization effluent stream in line 65 and a butane isomerization effluent stream in line 90 and feed them to the depropanizer column 70 as a combined depropanizer feed stream.

A depropanizer overhead stream is withdrawn from the depropanizer column 70 in a depropanizer overhead line 72 and condensed in a cooler and passed into a separator 74. A portion of the condensed depropanizer overhead stream is recycled to the depropanizer column 70 as reflux through a reflux line and the remaining portion of the condensed depropanizer overhead stream is withdrawn in a net depropanizer overhead line 76 as a propane stream. The propane stream in the line 76 may be charged as feed to the steam cracker 150 or to a paraffin dehydrogenation process (not shown) perhaps after separation of lighter components from the propane. A depropanizer off gas stream comprising C2– hydrocarbons and light gases is taken from the separator overhead in a depropanizer off-gas line 73. The depropanizer off gas in the off-gas overhead line 73 may be scrubbed (not shown) to remove chlorine if a chloride isomerization catalyst is in the butane isomerization unit 80 or the higher isomerization unit 60 and passed to fuel gas processing or sent to further processing for further recovery of hydrogen and/or ethane which can be used as steam cracking feed to the steam cracking unit 150.

The depropanized bottoms stream is withdrawn from the depropanizer column 70 through a bottoms line 78 from which a portion of the depropanized bottoms stream flows through a reboiler line 77, a reboiler heater and returns to the depropanizer column 70. The remaining portion of the depropanized bottoms flows through a net depropanized bottoms line 79 rich in C4-C7 normal and iso-paraffins, is cooled by heat exchange with the depropanizer feed stream in line 92 and is recycled to the feed line 10 to the adsorption separation unit 12 for separation of the normal paraffins from the non-normal paraffins. The C4-C7 hydrocarbon stream may be characterized as a C4+ hydrocarbon stream. In an embodiment, the entire C4-C7 paraffin stream is recycled to the adsorption separation unit 12. The depropanizer column 70 operates in bottoms temperature range of about 90 to about 150° C. and an overhead pressure range of about 1.3 to about 2.7 MPa and preferably about 1.7 to about 2.5 MPa.

Because the complete depropanized bottoms stream comprising C4+ hydrocarbons, specifically C4-C7 hydrocarbons, can be recycled to the adsorption separation unit 12, without having to separate normal butanes from iso-butanes in a dedicated deisobutanizer column, the process and apparatus 2 is much simplified.

In an embodiment, the propane stream in the net depropanizer overhead line 76 may be passed to a deethanizer column 110 to remove lighter materials from the propane stream before it is fed to the steam cracker 150 or subjected to paraffin dehydrogenation. The deethanizer column 110 separates the propane stream in line 76 into a deethanizer overhead stream comprising ethane and lighter materials and a deethanized propane bottoms stream comprising C3 paraffins in a single fractionation column.

A deethanizer overhead stream is withdrawn from the deethanizer column 110 in a deethanizer overhead line 112 and condensed in a cooler and passed into a separator 114. A condensed deethanizer overhead stream is recycled to the deethanizer column 110 as reflux through a reflux line. A net vaporous deethanizer overhead stream is withdrawn in a net deethanizer overhead line 113 as an ethane stream. The ethane stream in the deethanizer overhead line 113 may be joined by the depropanizer off gas stream comprising C2– hydrocarbons and light gases in the depropanizer off-gas line 73 to provide a mixed ethane stream in an ethane line 120. The mixed ethane stream in the line 120 may be charged as feed to the steam cracker 150 as is or further demethanized (not shown) to isolate a purer ethane stream for feed to the steam cracker while the demethanized overhead may be passed to fuel gas processing or sent to further processing for further recovery of hydrogen. The mixed ethane stream in the ethane line 120 may also be scrubbed (not shown) to remove chlorine if a chloride isomerization catalyst is in the butane isomerization unit 80 or the higher isomerization unit 60.

A deethanized propane stream is withdrawn from the deethanizer column 110 through a bottoms line 118 from which a portion of the deethanized propane stream flows through a reboiler line 117, a reboiler heater and returns to the deethanizer column 110. The remaining portion of the deethanized propane stream flows through a net deethanized bottoms line 119. The deethanized propane stream may be fed to the stream cracker 150, perhaps in line 40. The deethanizer column 110 operates in bottoms temperature range of about 100 to about 130° C. and an overhead pressure range of about 1.5 to about 3 MPa (gauge).

Figure 2:
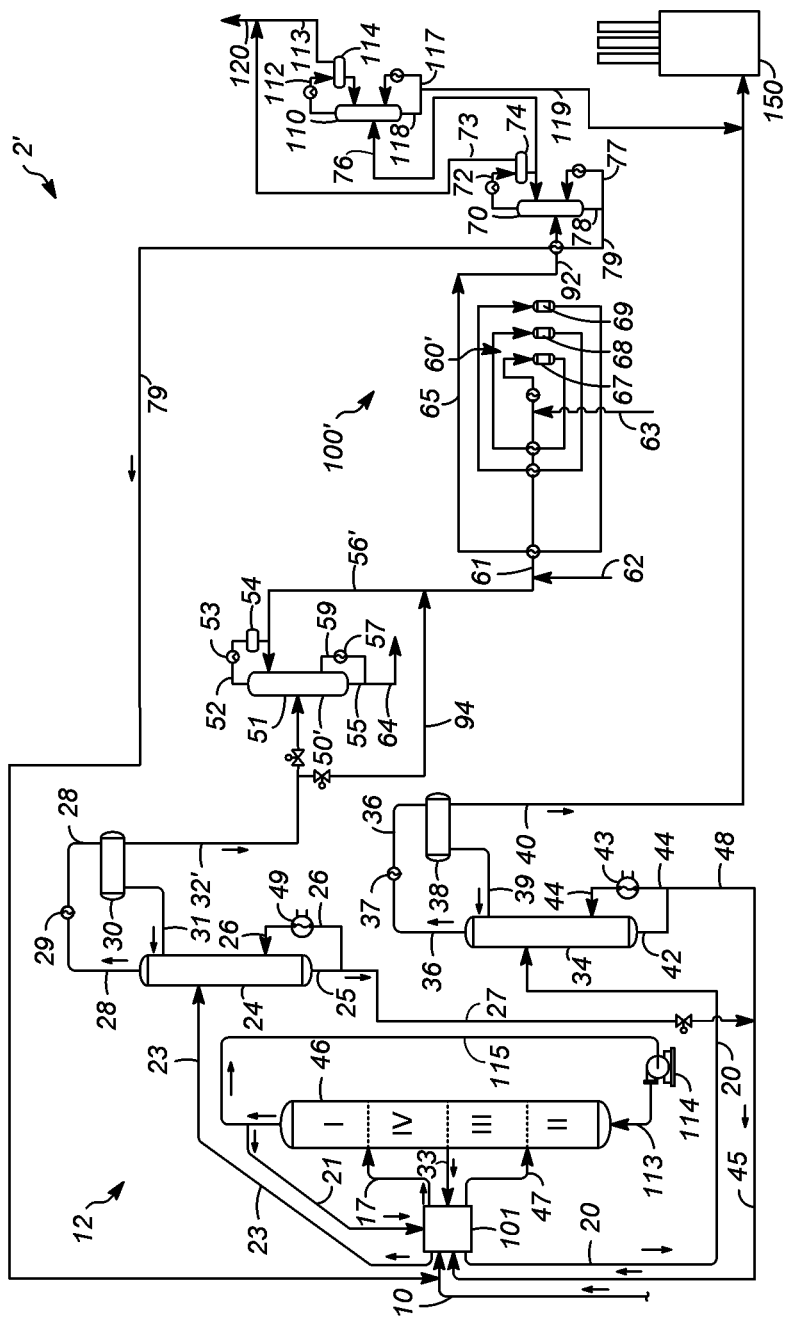
FIG. 2 is a schematic view of an alternate conversion unit of FIG. 1.

FIG. 2 shows an embodiment of a process and apparatus 2' which utilizes a single isomerization unit 60' in the isomerization zone 100'. Elements in FIG. 2 with the same configuration as in FIG. 1 will have the same reference numeral as in FIG. 1. Elements in FIG. 2 which have a different configuration as the corresponding element in FIG. 1 will have the same reference numeral but designated with a prime symbol ('). The configuration and operation of the embodiment of FIG. 2 is essentially the same as in FIG. 1.

In the alternative embodiment of FIG. 2, the process 2' installs an optional raffinate splitter column 50' downstream of the adsorbent separation vessel 46 to separate the net raffinate overhead stream comprising non-normal paraffins in line 32' into a raffinate splitter overhead stream that is rich in isobutanes comprising an isobutane stream and a bottoms stream rich in C6 cyclics and comprise a C6 cyclics and C7+ hydrocarbon stream. A control valve on line 32' admits the net raffinate overhead stream into the raffinate splitter column 50'. The raffinate splitter overhead stream may be rich in isopentane and may comprise an isopentane stream. The raffinate splitter overhead stream may also be rich in isohexane and may comprise an isohexane stream. The raffinate splitter overhead stream may be characterized as an isoalkane stream. The net raffinate overhead stream comprising non-normal paraffins in line 32' may also be separated into a C6 cyclic and C7+ hydrocarbons stream in the raffinate splitter column 50'. Since the non-normal paraffin stream in line 32' contains little n-hexane with a normal boiling point of 69° C. because it is removed in the adsorption separation vessel 46, the separation of C6 cyclics from iso-paraffins is simplified. The lightest C6 cyclic hydrocarbon is methylcyclopentane having a normal boiling point of 72° C. whereas iso-C6 paraffins normally boil at 50-64° C. Hence, the proper ordering of separation steps obviates a difficult split between normal hexane and methylcyclopentane that would be capital and operationally intensive and result in a loss of much of the normal hexane, which is a valuable steam cracker feed.

The raffinate splitter overhead stream in the raffinate splitter net overhead line 52 separated from the non-normal paraffin stream in line 32' is rich in isobutanes, isopentanes and/or isohexanes. The raffinate splitter overhead stream is withdrawn in a raffinate splitter overhead line 52 from an overhead of the raffinate splitter column 50' and passed through a cooler 53 and into a separator 54. A portion of the raffinate splitter overhead stream is recycled to the raffinate splitter column 50' as reflux through a reflux line and the remaining portion of the raffinate splitter overhead stream is withdrawn in a net raffinate splitter overhead line 56'. The raffinate splitter overhead stream taken in the net raffinate splitter overhead line 56' from the non-normal paraffin stream in line 32' may be charged as a first and perhaps only isomerization feed stream to an isomerization unit 60' to increase its normal-alkane concentration.

The raffinate splitter bottoms stream is withdrawn from raffinate splitter column 50' through a bottoms line 55 from which a portion of the raffinate splitter bottoms flows through a reboiler line 59, a reboiler heater 57 and returns to the raffinate splitter column 50'. The remaining portion of the raffinate splitter bottoms stream flows through a net splitter bottoms line 64 as a cyclic hydrocarbon stream rich in cyclic C6 hydrocarbons and benzene and particularly rich in methylcyclopentane. The cyclic paraffins stream in the net splitter bottoms line 64 can be taken to a reforming unit to produce aromatic hydrocarbons or sent to the steam cracker 150. Any C4+ hydrocarbons produced from steam cracking or reforming the cyclic paraffins stream can be recycled to the adsorption separation unit 12. The raffinate splitter column 50 operates in bottoms temperature range of about 124 to about 154° C. and an overhead pressure range of about 0 to about 138 kPa (gauge).

It should also be noted that in a further embodiment, a control valve on line 32' can be shut and a control valve on a bypass line 94 be opened to bypass the raffinate splitter column 50' in the bypass line to permit some or the entire non-normal stream in the net raffinate line 32' to enter the single isomerization unit 60' without removing C6 cyclics and C7+ hydrocarbons from the single isomerization feed stream in line 62 in the event that the single isomerization catalyst can catalyze sufficient isomerization to normal C4-C6 paraffins.

The non-normal, non-cyclic paraffin rich stream in the raffinate splitter net overhead line 56' and/or the non-normal stream from the net raffinate line 32' and bypassed in bypass line 94 may be combined with a hydrogen stream in a hydrogen line 62 and heated by heat exchange with reactor effluent and fed to a single isomerization unit 60'. In the single isomerization unit 60', isobutane, isopentane and/or isohexane, in the presence of hydrogen provided by hydrogen line 62 and an isomerization catalyst, are converted to increase the concentration of normal paraffins: ethane, propane, normal butane, normal pentane and normal hexane. Three reactions promote the production of normal paraffin-iso-paraffin disproportionation reactions, reverse isomerization of iso-paraffins, and paraffin hydrocracking reactions.

Cracking of some of the paraffins can occur in the single isomerization unit 60' to produce C4– paraffins. Moreover, the conversion of isobutane, isopentane and/or isohexane increases significantly via disproportionation reactions due to the fact that the non-normal, non-cyclic paraffin rich stream in the intermediate raffinate overhead line 56' are passed into the single isomerization unit 60' lean in cyclic C6 hydrocarbons. It is believed that the paraffin disproportionation reactions occur by the combination of two iso-paraffins followed by scission into one lighter hydrocarbon and one heavier hydrocarbon. For example, two isopentanes can combine and form an isobutane and an isohexane in the presence of hydrogen. The isobutanes can further react via disproportionation to form a propanes and isopentanes. A significant portion of the produced isobutanes also converts to normal butanes via isomerization reactions in the isomerization zone. Production of normal propane and butane via disproportionation and isomerization reactions occurs with low production of low-value undesired methane as a cracked product. Thus, there is an increase in the overall yield of the normal paraffins in the single isomerization unit 60'.

In the single isomerization unit 60', hydrocracking of the isopentane and/or isohexane occurs to produce methane, ethane, propane, and isobutane. The isobutane can further react via disproportionation reactions and/or isomerization to further produce normal paraffins.

The single isomerization catalyst is capable of isomerizing all of isobutane, isopentane and isohexane to normal hydrocarbons. The isomerization catalyst in the single isomerization unit 60' may include chlorided alumina, sulfated zirconia, tungstated zirconia or zeolite-containing isomerization catalysts. The isomerization catalyst may be amorphous, e.g., based upon amorphous alumina, or zeolitic. A zeolitic catalyst would still normally contain an amorphous binder. The catalyst may comprise a sulfated zirconia and platinum as described in U.S. Pat. No. 5,036,035 and EP 0666109 A1 or a platinum group metal on chlorided alumina as described in U.S. Pat. Nos. 5,705,730 and 6,214,764. Another suitable catalyst is described in U.S. Pat. No. 5,922,639. U.S. Pat. No. 6,818,589 discloses a catalyst comprising a tungstated support of an oxide or hydroxide of a Group IVB (IUPAC 4) metal, preferably zirconium oxide or hydroxide, at least a first component which is a lanthanide element and/or yttrium component, and at least a second component being a platinum-group metal component. An advantage of a non-chlorided catalyst, such as a sulfated zirconia catalyst, is the absence of chloride omitting further treatment of the effluent streams from the single isomerization unit 60'. If chlorided alumina catalyst is used as the isomerization catalyst, a chloriding agent in line 63 will be added to the higher isomerization feed stream 61.

The isomerization process conditions in the single isomerization unit 60' include an average reactor temperature usually ranging from about 40° to about 250° C. Reactor operating pressures generally range from about 100 kPa to 10 MPa absolute. Liquid space velocities range from about 0.2 to about 25 volumes of hydrocarbon feed per hour per volume of catalyst. Hydrogen is admixed with or remains with the higher isomerization feed to the single isomerization unit 60' to provide a mole ratio of hydrogen to hydrocarbon feed of from about 0.01 to 20. The hydrogen may be supplied totally from outside the process or supplemented by hydrogen recycled to the feed after separation from higher isomerization reactor effluent.

Contacting within the single isomerization unit 60 may be effected using the single isomerization catalyst in a fixed-bed system, a moving-bed system, a fluidized-bed system, or in a batch-type operation. The reactants may be contacted with the bed of higher isomerization catalyst particles in upward, downward, or radial-flow fashion. The reactants may be in the liquid phase, a mixed liquid-vapor phase, or a vapor phase when contacted with the higher isomerization catalyst particles, with a mixed phase or vapor phase being preferred. The single isomerization unit 60' may be in a single reactor 66 or in two or more separate isomerization reactors 67, 68, and 69 with suitable means therebetween to ensure that the desired isomerization temperature is maintained at the entrance to each reactor.

The reactions in the single isomerization unit 60' generate an exotherm across the reactors so the single isomerization effluent streams need to be cooled between reactors. For example, a first single isomerate stream from a first isomerization reactor 67 may be heat exchanged with the single isomerization feed stream in the single isomerization feed line 61 comprising the non-normal, non-cyclic paraffin rich stream mixed with hydrogen to cool the single isomerate and heat the single isomerization feed stream. Moreover, a second single isomerate stream from a second single isomerization reactor 68 may be heat exchanged with the single isomerization feed stream comprising the non-normal, non-cyclic paraffin rich stream mixed with hydrogen upstream of the heat exchange with the first single isomerate steam to cool the single isomerate stream and heat the single isomerization feed stream. Additionally, a third isomerate stream from the third isomerization reactor 69 may be heat exchanged with the single isomerization feed stream comprising non-normal, non-cyclic paraffin rich stream mixed with hydrogen upstream of the heat exchange with the second single isomerate stream to cool the single isomerate and heat the single isomerization feed stream. Since hydrocracking reactions are accompanied by hydrogenation reactions that are very exothermic, two to five single isomerization reactors in sequence enable improved control of individual reactor temperatures and partial catalyst replacement without a process shutdown. A single isomerization effluent stream comprising an increased concentration of normal paraffins exits the last single isomerization reactor 69 in the single isomerization unit 60' in a single isomerization effluent line 65.

The single isomerization effluent stream in the single isomerization effluent line 65 may be separated in a depropanizer 70 and further processed as explained with regard to FIG. 1.

Figure 3:
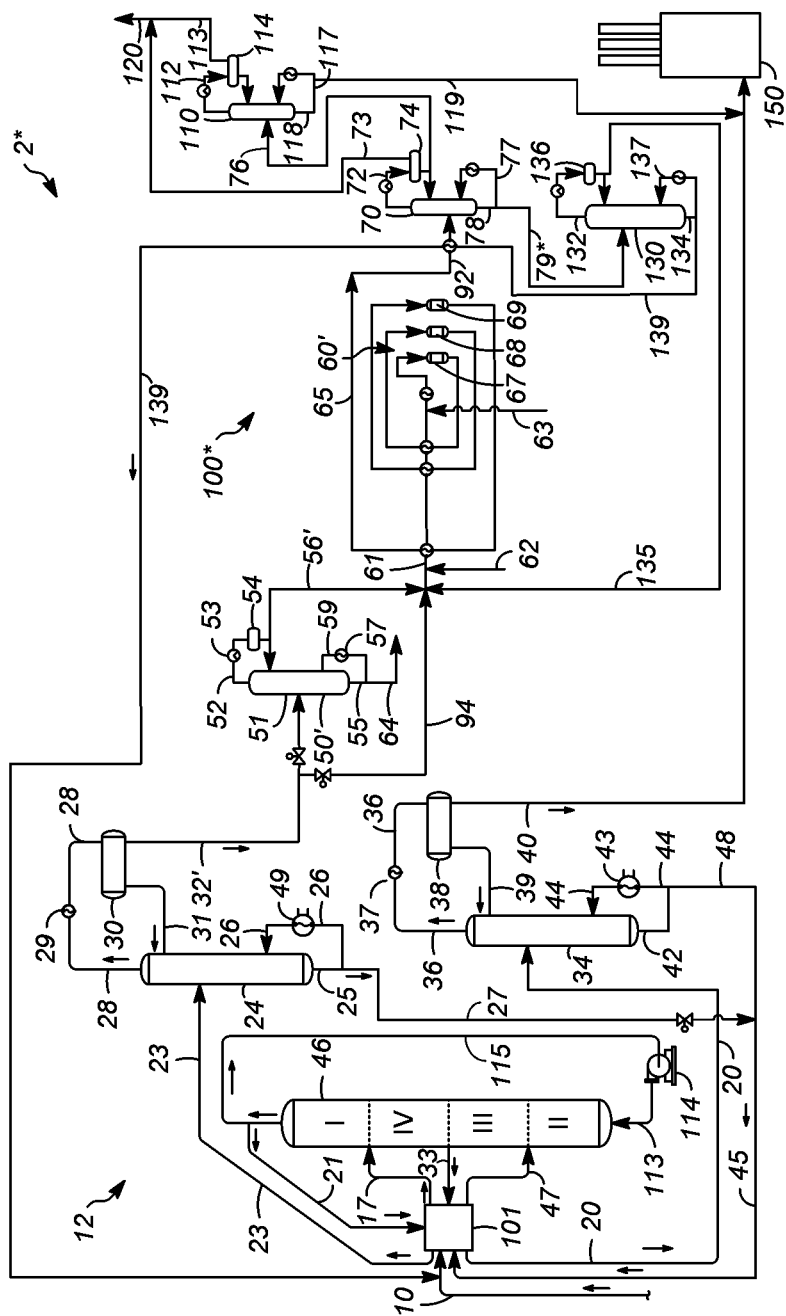
FIG. 3 is a schematic view of an alternate conversion unit of FIG. 2.

FIG. 3 shows an embodiment of a process and apparatus 2\* which utilizes a deisobutanizer column 130 to recycle isobutanes to an isomerization unit 100\* and normal butanes and heavier paraffins to the adsorbent separation unit 12. Elements in FIG. 3 with the same configuration as in FIG. 2 will have the same reference numeral as in FIG. 2. Elements in FIG. 3 which have a different configuration as the corresponding element in FIG. 2 will have the same reference numeral but designated with an asterisk symbol (\*). The configuration and operation of the embodiment of FIG. 3 is essentially the same as in FIG. 2. Although not shown, the embodiment of FIG. 3 can also be easily adaptable to the embodiment of FIG. 1.

In an embodiment, the remaining portion of the depropanized bottoms stream in the net depropanized bottoms line 79\* rich in C4-C7 normal and iso-paraffins characterized as a C4+ paraffin stream is fed to a deisobutanizer column 130 to separate the C4+ stream into an iso-C4 paraffin rich overhead stream in an overhead line 132 and a normal C4 and C5-C7 paraffin rich bottoms stream in a bottoms line 134. The deisobutanizer overhead stream rich in isobutane is withdrawn from the deisobutanizer column 130 in a deisobutanizer overhead line 132 and fully condensed in a cooler and passed into a separator 136. A portion of the condensed deisobutanizer overhead stream is recycled to the deisobutanizer column 130 as reflux through a reflux line and the remaining condensed deisobutanizer overhead stream is taken as an isobutane rich stream in a deisobutanizer net overhead line 135. The isobutane stream may be fed to the isomerization unit 100\* to increase the concentration of normal butane paraffins in the isobutane stream in the deisobutanizer net overhead line 135. In an aspect, the deisobutanizer net overhead stream is recycled to the isomerization unit 100\* after mixing with the raffinate splitter overhead stream in the net raffinate splitter overhead line 56' or some or the entire non-normal stream in the net raffinate line bypass line 94. If the embodiment of FIG. 3 is applied to the embodiment of FIG. 1, the isobutane stream in the deisobutanizer net overhead line 135 would be combined with the raffinate splitter overhead stream in the net raffinate splitter overhead line 56 of FIG. 1.

The deisobutanized bottoms stream is withdrawn from the deisobutanizer column 130 through a bottoms line 134 from which a portion of the deisobutanized bottoms stream flows through a reboiler line 137, a reboiler heater and returns to the deisobutanizer column 130. The remaining portion of the deisobutanized bottoms flows through a net deisobutanized bottoms line 139 which is rich in normal butane and heavier C5-C7 paraffins. Thus, a normal butane and C5-C7 paraffin rich stream is separated from isobutanes and recycled to the adsorbent separation vessel 46 in line 139 after heat exchange with the isomerization stream 92. The deisobutanizer column 130 operates in bottoms temperature range of about 50 to about 100° C. and an overhead pressure range of about 400 to about 800 kPa (gauge).

Alternatively, the raffinate overhead stream in the overhead line 28 may be fully condensed and fully refluxed in line 31 and the raffinate stream in line 32' be taken from a side cut (not shown) from the raffinate column 24.

Figure 4:
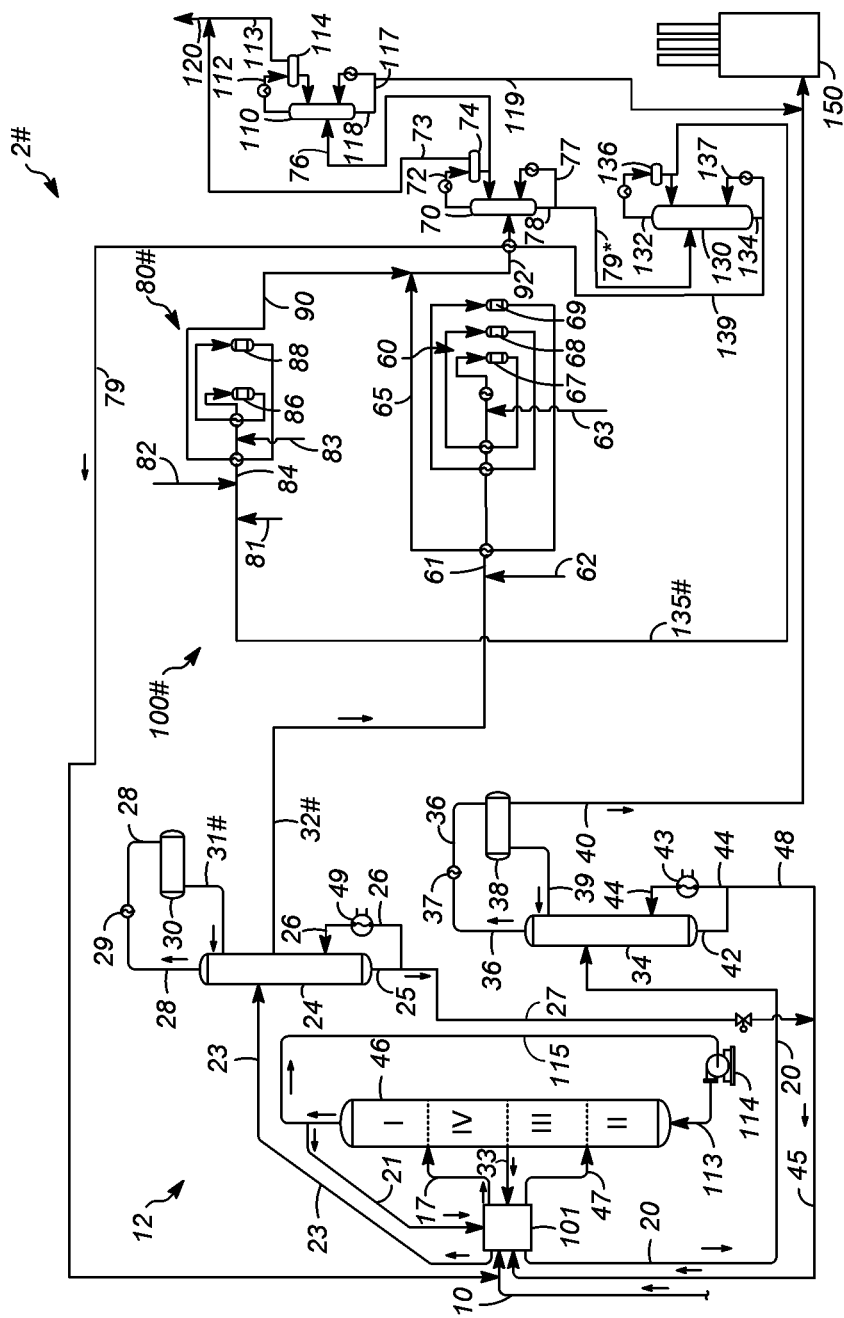
FIG. 4 is a schematic view of an alternate conversion unit of FIGS. 1 and 3.

FIG. 4 shows an embodiment of a process and apparatus 2# which recycles the isobutane stream in the deisobutanizer net overhead line 135# to a first, butane isomerization unit 80#. Elements in FIG. 4 with the same configuration as in FIG. 1 or 3 will have the same reference numeral as in FIG. 1 or 3. Elements in FIG. 4 which have a different configuration as the corresponding element in FIG. 1 or 3 will have the same reference numeral but designated with a hashtag symbol (#). The configuration and operation of the embodiment of FIG. 4 is essentially the same as in FIGS. 1 and 3.

The deisobutanizer net overhead line 135# may be combined with a first hydrogen stream in a first hydrogen line 82 and optionally a fresh isobutane stream in a fresh isobutane line 81 to provide an isobutane isomerization feed stream in an isobutane isomerization feed line 84. The isobutane isomerization feed stream is heated by heat exchange with an isobutane isomerization effluent stream and isomerized in the first, butane isomerization unit 80. In the first, butane isomerization unit 80, the isobutane paraffins, in the presence of hydrogen provided by the hydrogen line 83 and a butane isomerization catalyst, are converted into normal butane to attain equilibrium levels of normal butane as described for FIG. 1. A first, butane isomerization effluent stream comprising an increased concentration of normal paraffins exits the last reactor in the butane isomerization unit 80# in a butane isomerization effluent line 90. The butane isomerization effluent stream in line 90 may be fed to a depropanizer column 70 in a depropanizer feed line 92 after it is combined with a higher isomerization effluent stream in line 65.

In an embodiment, the raffinate splitter column 51 may be eliminated. The raffinate overhead stream in the raffinate overhead line 28 may be fully condensed and fully refluxed in line 31# and the raffinate stream in an intermediate line 32# be taken from a side cut from the raffinate column 24.

A higher isoalkane stream may be taken in the intermediate line 32# from the side of the raffinate column 24 and fed as a second, higher isoalkane isomerization feed stream to a second, higher isomerization unit 60 to increase its normal alkane concentration. Particularly, the higher isomerization unit 60 increases the concentration of normal pentanes and/or normal hexanes.

The remainder of FIG. 4 operates and is configured as described for FIGS. 1 and 3.

SPECIFIC EMBODIMENTS

While the following is described in conjunction with specific embodiments, it will be understood that this description is intended to illustrate and not limit the scope of the preceding description and the appended claims.

A first embodiment of the disclosure is a process for increasing the concentration of normal paraffins in a feed stream comprising separating a naphtha feed stream into a normal paraffin stream and a non-normal paraffin stream; isomerizing an isomerization feed stream taken from the non-normal paraffin stream over an isomerization catalyst to convert non-normal paraffins to normal paraffins and produce an isomerization effluent stream; separating the isomerization effluent stream into a propane stream and a C4+ hydrocarbon stream; and recycling the C4+ hydrocarbon stream to the step of separating a naphtha feed stream. An embodiment of the disclosure is one, any or all of prior embodiments in this paragraph up through the first embodiment in this paragraph wherein the C4+ hydrocarbon stream is a C4-C6 hydrocarbon stream. An embodiment of the disclosure is one, any or all of prior embodiments in this paragraph up through the first embodiment in this paragraph further comprising separating the non-normal paraffin stream into an isobutane stream and an isopentane stream and taking the isobutane stream as a first isomerization feed stream and taking the isopentane stream as a second isomerization feed stream and isomerizing the second isomerization feed stream over a second isomerization catalyst to convert isopentanes to normal pentanes and produce a second isomerization effluent stream. An embodiment of the disclosure is one, any or all of prior embodiments in this paragraph up through the first embodiment in this paragraph further comprising separating the second isomerization effluent stream into a propane stream and a C4+ hydrocarbon stream optionally in a single column and recycling the C4+ hydrocarbon stream to the step of separating a naphtha feed stream. An embodiment of the disclosure is one, any or all of prior embodiments in this paragraph up through the first embodiment in this paragraph further comprising separating the second isomerization effluent stream in the same step as separating the first isomerization effluent stream. An embodiment of the disclosure is one, any or all of prior embodiments in this paragraph up through the first embodiment in this paragraph further comprising separating the propane stream in a deethanizer column to provide and a deethanized propane stream and transporting the deethanized propane stream to either a paraffin dehydrogenation unit or a steam cracker. An embodiment of the disclosure is one, any or all of prior embodiments in this paragraph up through the first embodiment in this paragraph further comprising producing an ethane stream in the deethanizer column and transporting the ethane stream to a steam cracker. An embodiment of the disclosure is one, any or all of prior embodiments in this paragraph up through the first embodiment in this paragraph further comprising deisobutanizing the C4+ hydrocarbon stream to produce an isobutane stream and a deisobutanized C4+ stream; recycling the isobutane stream to the isomerization reactor and recycling the deisobutanized C4+ stream to the step of separating a naphtha feed stream. An embodiment of the disclosure is one, any or all of prior embodiments in this paragraph up through the first embodiment in this paragraph further comprising separating a methylcyclopentane stream from the non-normal paraffin stream and reforming or steam cracking the methylcyclopentane stream. An embodiment of the disclosure is one, any or all of prior embodiments in this paragraph up through the first embodiment in this paragraph further comprising feeding the normal paraffin stream to a steam cracker. An embodiment of the disclosure is one, any or all of prior embodiments in this paragraph up through the first embodiment in this paragraph wherein the step of separating the naphtha feed stream into the normal paraffins stream from the non-normal paraffins stream comprises extracting the normal paraffins by use of an adsorbent. An embodiment of the disclosure is one, any or all of prior embodiments in this paragraph up through the first embodiment in this paragraph wherein the extracting step produces a raffinate stream comprising non-normal paraffins and desorbent and further comprising separating the raffinate stream into a raffinate desorbent stream and the non-normal paraffin stream. An embodiment of the disclosure is one, any or all of prior embodiments in this paragraph up through the first embodiment in this paragraph wherein the extracting step produces an extract stream comprising normal paraffins and desorbent and further comprising separating the extract stream into an extract desorbent stream and the normal paraffin stream.

A second embodiment of the disclosure is a process for increasing the concentration of normal paraffins in a feed stream comprising separating a naphtha feed stream into a normal paraffin stream and a non-normal paraffin stream; separating the non-normal paraffin stream into an isobutane stream and an isopentane stream; isomerizing the isobutane stream over a first isomerization catalyst to convert isobutanes to normal butanes and produce a first isomerization effluent stream; and isomerizing the isopentane stream over a second isomerization catalyst to convert isopentanes to normal pentanes and produce a second isomerization effluent stream. An embodiment of the disclosure is one, any or all of prior embodiments in this paragraph up through the second embodiment in this paragraph further comprising separating the first isomerization effluent stream into a propane stream and a C4+ hydrocarbon stream optionally in a single column; recycling the C4+ hydrocarbon stream to the step of separating a naphtha feed stream; separating the second isomerization effluent stream into a propane stream and a C4+ hydrocarbon stream optionally in a single column; and recycling the C4+ stream to the step of separating a naphtha feed stream. An embodiment of the disclosure is one, any or all of prior embodiments in this paragraph up through the second embodiment in this paragraph further comprising separating the first isomerization effluent stream and the second isomerization effluent stream together and recycling the C4+ hydrocarbon stream to the step of separating a naphtha feed stream. An embodiment of the disclosure is one, any or all of prior embodiments in this paragraph up through the second embodiment in this paragraph wherein the step of separating the naphtha feed stream into the normal paraffins stream from the non-normal paraffins stream comprises extracting the normal paraffins by use of an adsorbent; and further comprising producing a raffinate stream comprising non-normal paraffins and desorbent and separating the raffinate stream into a raffinate desorbent stream and the non-normal paraffin stream. An embodiment of the disclosure is one, any or all of prior embodiments in this paragraph up through the second embodiment in this paragraph further comprising producing an extract stream comprising normal paraffins and desorbent and separating the extract stream into an extract desorbent stream and the normal paraffin stream.

A third embodiment of the disclosure is a process for increasing the concentration of normal paraffins in a feed stream comprising extracting normal paraffins from a naphtha feed stream comprising C4-C7 hydrocarbons by use of an adsorbent into an extract stream and producing a raffinate stream comprising non-normal paraffins; taking a non-normal paraffin stream from the raffinate stream; isomerizing an isomerization feed stream taken from the non-normal paraffin stream over an isomerization catalyst to convert non-normal paraffins to normal paraffins and produce an isomerization effluent stream; separating the isomerization effluent stream into a propane stream and a C4+ hydrocarbon stream; deisobutanizing the C4+ hydrocarbon stream to produce an isobutane stream and a deisobutanized C4+ stream; recycling the isobutane stream to the isomerization step; and recycling the C4+ hydrocarbon stream to the step of extracting normal paraffins from a naphtha feed stream. An embodiment of the disclosure is one, any or all of prior embodiments in this paragraph up through the third embodiment in this paragraph further comprising separating the propane stream in a deethanizer column to provide and a deethanized propane stream and transporting the deethanized propane stream to either a paraffin dehydrogenation unit or a steam cracker.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for increasing the concentration of normal paraffins in a feed stream comprising:
    separating a naphtha feed stream into a normal paraffin stream and a non-normal paraffin stream;
    separating said non-normal paraffin stream into an isobutane stream and an isopentane stream;
    isomerizing said isobutane stream over a first isomerization catalyst in an isomerization reactor to convert isobutanes to normal butanes and produce a first isomerization effluent stream; and
    isomerizing said isopentane stream over a second isomerization catalyst to convert isopentanes to normal pentanes and produce a second isomerization effluent stream;
    separating said first isomerization effluent stream and second isomerization effluent stream into a propane stream and a C4+ hydrocarbon stream; and
    recycling said C4+ hydrocarbon stream to the step of separating a naphtha feed stream.

2. The process of claim 1 wherein said C4+ hydrocarbon stream is a C4-C6 hydrocarbon stream.

3. The process of claim 1 further comprising separating said second isomerization effluent stream into a propane stream and a C4+ hydrocarbon stream optionally in a single column and recycling said C4+ hydrocarbon stream to the step of separating a naphtha feed stream.

4. The process of claim 3 further comprising separating said second isomerization effluent stream in the same step as separating said first isomerization effluent stream.

5. The process of claim 1 further comprising separating said propane stream in a deethanizer column to provide and a deethanized propane stream and transporting said deethanized propane stream to either a paraffin dehydrogenation unit or a steam cracker.

6. The process of claim 5 further comprising producing an ethane stream in said deethanizer column and transporting the ethane stream to a steam cracker.

7. The process of claim 1 further comprising deisobutanizing said C4+ hydrocarbon stream to produce an isobutane stream and a deisobutanized C4+ stream; recycling said isobutane stream to the isomerization reactor and recycling said deisobutanized C4+ stream to the step of separating a naphtha feed stream.

8. The process of claim 1 further comprising separating a methylcyclopentane stream from said non-normal paraffin stream and reforming or steam cracking said methylcyclopentane stream.

9. The process of claim 1 further comprising feeding said normal paraffin stream to a steam cracker.

10. The process of claim 1 wherein the step of separating the naphtha feed stream into the normal paraffins stream from the non-normal paraffins stream comprises extracting said normal paraffins by use of an adsorbent.

11. The process of claim 9 wherein said extracting step produces a raffinate stream comprising non-normal paraffins and desorbent and further comprising separating said raffinate stream into a raffinate desorbent stream and said non-normal paraffin stream.

12. The process of claim 9 wherein said extracting step produces an extract stream comprising normal paraffins and desorbent and further comprising separating said extract stream into an extract desorbent stream and said normal paraffin stream.

13. A process for increasing the concentration of normal paraffins in a feed stream comprising:
    separating a naphtha feed stream into a normal paraffin stream and a non-normal paraffin stream;
    separating said non-normal paraffin stream into an isobutane stream and an isopentane stream;
    isomerizing said isobutane stream over a first isomerization catalyst to convert isobutanes to normal butanes and produce a first isomerization effluent stream; and
    isomerizing said isopentane stream over a second isomerization catalyst to convert isopentanes to normal pentanes and produce a second isomerization effluent stream.

14. The process of claim 13 further comprising:
    separating said first isomerization effluent stream into a propane stream and a C4+ hydrocarbon stream optionally in a single column;
    recycling said C4+ hydrocarbon stream to the step of separating a naphtha feed stream;
    separating said second isomerization effluent stream into a propane stream and a C4+ hydrocarbon stream optionally in a single column; and
    recycling said C4+ stream to the step of separating a naphtha feed stream.

15. The process of claim 14 further comprising separating the first isomerization effluent stream and the second isomerization effluent stream together and recycling the C4+ hydrocarbon stream to the step of separating a naphtha feed stream.

16. The process of claim 13 wherein the step of separating the naphtha feed stream into the normal paraffins stream from the non-normal paraffins stream comprises extracting said normal paraffins by use of an adsorbent; and further comprising producing a raffinate stream comprising non-normal paraffins and desorbent and separating said raffinate stream into a raffinate desorbent stream and said non-normal paraffin stream.

17. The process of claim 16 further comprising producing an extract stream comprising normal paraffins and desorbent and separating said extract stream into an extract desorbent stream and said normal paraffin stream.

18. A process for increasing the concentration of normal paraffins in a feed stream comprising:
- extracting normal paraffins from a naphtha feed stream comprising C4-C7 hydrocarbons by use of an adsorbent into an extract stream and producing a raffinate stream comprising non-normal paraffins;
- taking a non-normal paraffin stream from said raffinate stream;
- isomerizing an isomerization feed stream taken from the non-normal paraffin stream over an isomerization catalyst to convert non-normal paraffins to normal paraffins and produce an isomerization effluent stream;
- separating said isomerization effluent stream into a propane stream and a C4+ hydrocarbon stream;
- deisobutanizing said C4+ hydrocarbon stream to produce an isobutane stream and a deisobutanized C4+ stream;
- recycling said isobutane stream to the isomerization step; and
- recycling said C4+ hydrocarbon stream to the step of extracting normal paraffins from a naphtha feed stream.

19. The process of claim 18 further comprising separating said propane stream in a deethanizer column to provide and a deethanized propane stream and transporting said deethanized propane stream to either a paraffin dehydrogenation unit or a steam cracker.

* * * * *